(12) United States Patent
Ouchi

(10) Patent No.: US 7,458,973 B2
(45) Date of Patent: Dec. 2, 2008

(54) HIGH-FREQUENCY SNARE FOR ENDOSCOPE

(75) Inventor: Teruo Ouchi, Saitama-ken (JP)

(73) Assignee: Hoya Corporation, Tokyo (JP)

( * ) Notice: Subject to any disclaimer, the term of this patent is extended or adjusted under 35 U.S.C. 154(b) by 474 days.

(21) Appl. No.: 11/218,779

(22) Filed: Sep. 6, 2005

(65) Prior Publication Data

US 2006/0052775 A1    Mar. 9, 2006

(30) Foreign Application Priority Data

Sep. 6, 2004    (JP) .............................. 2004-257891

(51) Int. Cl.
*A61B 18/14* (2006.01)
*H01R 43/00* (2006.01)

(52) U.S. Cl. .......................................... 606/47; 29/868
(58) Field of Classification Search ............. 606/46–47; 29/868

See application file for complete search history.

(56) References Cited

U.S. PATENT DOCUMENTS

| | | | |
|---|---|---|---|
| 3,272,962 A * | 9/1966 | Mauskapf | 219/137 R |
| 6,224,611 B1 | 5/2001 | Ouchi | |
| 6,245,078 B1 | 6/2001 | Ouchi | |
| 6,299,612 B1 * | 10/2001 | Ouchi | 606/47 |

2005/0131424 A1    6/2005 Ouchi

FOREIGN PATENT DOCUMENTS

| | | |
|---|---|---|
| JP | 5-54343 | 8/1993 |
| JP | 10-165406 | 6/1998 |
| JP | 2000-83963 | 3/2000 |
| JP | 2002-153484 | 5/2002 |

OTHER PUBLICATIONS

English language Abstract of JP 5-54343.
English language Abstract of JP 10-165406.
English language Abstract of JP 2000-83963.
U.S. Appl. No. 11/218,778 to Ouchi.

* cited by examiner

*Primary Examiner*—Lee S Cohen
(74) *Attorney, Agent, or Firm*—Greenblum & Bernstein, P.L.C.

(57) ABSTRACT

A high-frequency snare for an endoscope includes an electrically insulating sheath, an operation wire slidably inserted through the sheath, a plurality of resilient twisted wires. Proximal ends of the plurality of twisted wires are connected to the distal end of the operation wire. Distal ends of the plurality of twisted wires are deposited with each other within an atmosphere of inactive gas. A proximal end side of the deposited ends of the plurality of wires being connected together with a metallic connecting member. When the operation wire is operated to withdraw at least proximal side portions of the plurality of twisted wires, the twisted wires are tucked. The plurality of twisted wires are expanded to form a loop with resilience thereof when the plurality of twisted wires are protruded from the sheath.

5 Claims, 4 Drawing Sheets

HIGH-FREQUENCY SNARE FOR ENDOSCOPE

BACKGROUND OF THE INVENTION

The present invention relates to a high-frequency snare for an endoscope, which is inserted in a forceps channel of the endoscope and used for endoscopic excision of mucous membrane, and a method of forming such a high-frequency snare.

The high-frequency snare for the endoscope is typically formed such that a plurality of resilient metal wires are connected at their proximal and distal ends, to form a loop. When the connected wires are withdrawn inside a sheath, which has electrically insulating property, the wires resiliently deform and the loop is tucked, while when the wires are protruded from the sheath, the loop expand its full state due to the resilient property of the wires.

If a single line metallic wire is used for each of the plurality of wires forming the high-frequency snare, the resiliency may be too strong and may cause a problem when in use. Therefore, typically, as each wire for the snare, a twisted wire consisting of a plurality of thin wires which are twisted to form a single line of wire is used. At each end, the plurality of thin wires are connected by silver brazing, laser welding or plasma welding. Examples of such configurations are disclosed in Japanese Patent Provisional Publication No. P2000-83963A and Japanese Patent Publication No. H5-54343.

The high-frequency snare for the endoscope is typically used for tightly binding a polyp and cut it out by applying a high-frequency current to the snare. Recently, however, as an endoscopic mucous membrane excision is performed. In such a case, by use of a tip connected portion of the resilient wires, which portion is protruded frontward from the tip of the loop, the excision of the mucous membrane and detachment of the cut portion are performed, which have not yet been done before.

That is, the connecting portion of the wires that form the loop is used as the high-frequency electrode. By slightly inserting the connection portion in the mucous membrane and supplying a high-frequency current thereto, a portion where the connection portion of the resilient wires and the mucous surface is cauterized. Therefore, by moving the resilient wire with maintaining the above condition, the excision of the mucous membrane can be done.

When the mucous detachment is performed, the portion of the mucous which has been cut out by the excision operation is detached from the muscular layer, the connection portion of the resilient wires is inserted between the bottom side of the mucous membrane and the muscular layer. Then, the cut portion of the mucous membrane is removed with the high-frequency current being supplied to cut the tissues between the mucous membrane and the muscular layer.

When the high-frequency snare is used in the above way, however, electric sparks are generated between the connected portion of the resilient wires which serve as the high-frequency electrodes and the mucous membrane, and the temperature at that portion raises significantly.

If the wires are connected, at the connected portion, by silver brazing, the silver braze may be softened by the generated heat, and some of the wires may be disconnected, thereby breaking the snare loop.

If the wires are connected, at the connected portion, by the laser welding or the plasma welding, a very high temperature is applied to the wires when welded and the connected portion may become very brittle. Accordingly, if concentrated stress is generated when the mucous membrane is detached, the snare loop may easily be broken.

In addition, in the case of the laser welding or plasma welding, if the resilient wire consists of a single wire, the resilient wire is damaged little, while the wire is a twisted wire, relatively large damage is applied to the twisted wire as each wire segment has heated to a high temperature and it is difficult to carry out the welding operation.

SUMMARY OF THE INVENTION

The present invention is advantageous in that an improved high-frequency snare and a method of producing such a snare are provided. According to aspects of the invention, end portions of a plurality of resilient wires, each being formed by twisting thin wires, can be connected in a good condition without damaging each wire. The connection has durability against the high temperature due to the sparks at the high-frequency treatment, and also has durability against the concentric stress which is caused when the mucous membrane is removed.

According to an aspect of the present invention, a high-frequency snare for an endoscope including an electrically insulating sheath, an operation wire slidably inserted through the sheath, a plurality of resilient twisted wires is provided. Proximal ends of the plurality of twisted wires are connected to the distal end of the operation wire. Distal ends of the plurality of twisted wires are deposited with each other within an atmosphere of inactive gas. A proximal end side of the deposited ends of the plurality of wires being connected together with a metallic connecting member. When the operation wire is operated to withdraw at least proximal side portions of the plurality of twisted wires, the twisted wires are tucked. The plurality of twisted wires are expanded to form a loop with resilience thereof when the plurality of twisted wires are protruded from the sheath.

Optionally, the deposited ends of the plurality of wires may be formed to have an approximate shape of a hemisphere.

Optionally, the inactive gas may be one of argon and nitrogen.

Optionally, the deposited ends of the plurality of wires may be connected by one of plasma welding and laser welding.

Optionally, the proximal end side of the deposited ends of the plurality of wires may be connected by one of silver brazing and soldering.

According to another aspect of the present invention, a method of producing a high-frequency snare for an endoscope is provided. The high-frequency snare includes an electrically insulating sheath, an operation wire slidably inserted through the sheath and a plurality of resilient twisted wires, proximal ends of the plurality of twisted wires being connected to the distal end of the operation wire, distal ends of the plurality of twisted wires being connected with each other. The twisted wires are tucked when the operation wire is operated to withdraw at least proximal side portions of the plurality of twisted wires. The plurality of twisted wires are expanded to form a loop with resilience thereof when the plurality of twisted wires are protruded from the sheath. The method includes depositing the distal ends of the plurality of twisted wires within an atmosphere of inactive gas, and connecting a proximal end side of the deposited ends of the plurality of wires which are connected together with a metallic connecting member.

DETAILED DESCRIPTION OF THE EMBODIMENTS

Referring to the accompanying drawings, an embodiment of the present invention will be described.

Figure 1:
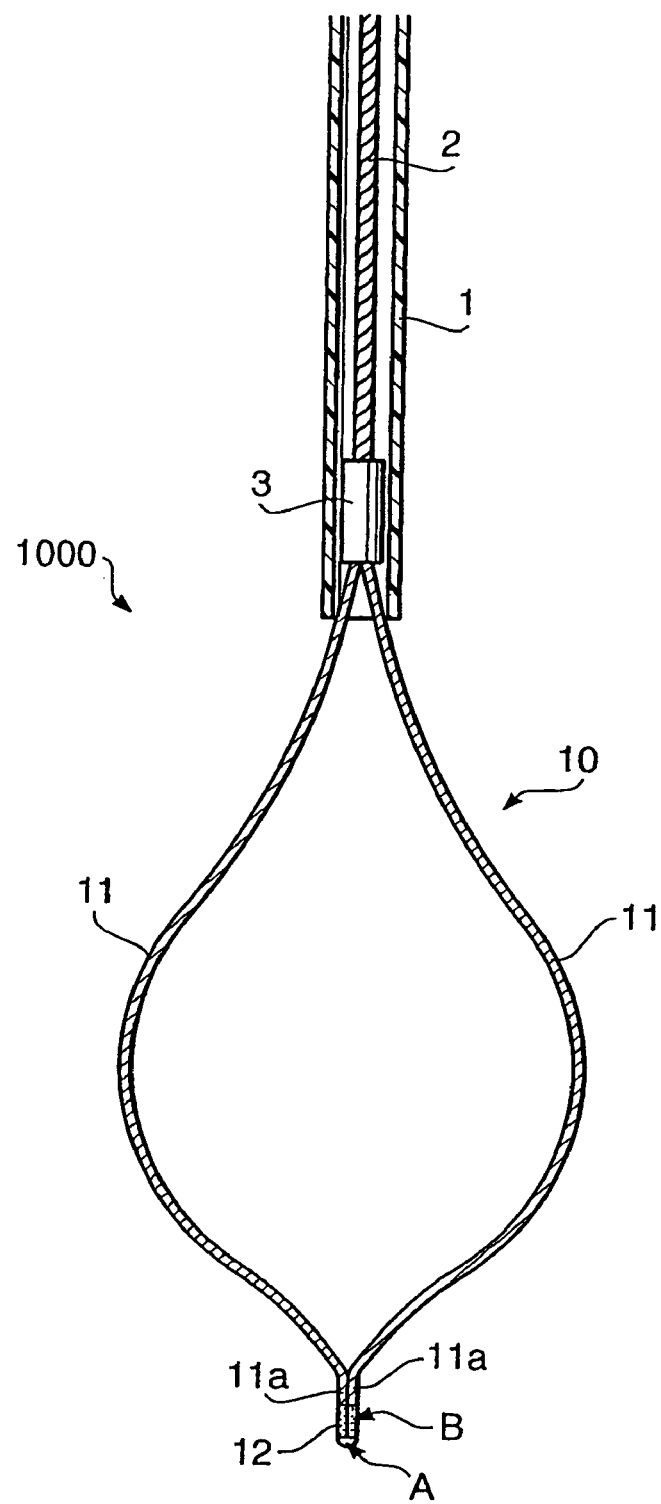
FIG. 1 is a cross-sectional side view of a tip portion of a high-frequency snare according to a first embodiment of the invention.

FIG. 1 is a cross-sectional side view of a tip portion of a high-frequency snare according to a first embodiment of the invention. The high-frequency snare 1000 is to be inserted in a forceps channel of an endoscope (not shown). The high-frequency snare 1000 includes a sheath 1 which is a flexible tubular member having electrically insulating property. For example, the sheath 1 is an elastic resin tube with a diameter of 2 mm made of ethylene tetrafluoride material. As shown in FIG. 1, an operation wire 2 (which is an electrically conductive wire consisting of a plurality of thin wires made of, for example, one of stainless steel) is inserted over the entire length of the sheath 1.

The operation wire 2 can be driven to move in the axial direction of the sheath 1 as an operation unit (not shown) connected to the proximal end of the wire 2 is operated.

A snare loop 10 is provided to the tip portion of the sheath 1. The snare loop 10 is formed such that two resilient wires 11 that are electrically conductive are connected at their proximal and distal ends to form a loop. Optionally, the snare loop 10 may consist of more than two resilient wires.

Each of the resilient wires 11 is formed with seven of thin stainless steel wires with the diameter of 0.13 mm, which are twisted to form a single line. It should be noted, however, the number of the thin wires is not limited to seven, but can be more or less than seven. Further, the diameter of the thin wire is not limited to 0.13 mm, either.

The proximal and distal ends of the looped resilient wires 11 are fixed with and silver-brazed to a connection pipe made of stainless steel which is at the tip of the operation wire 2. Thus, the resilient wires 11 are electrically conducted with the operation wire 2.

A tip portion 11a of the snare loop 10 is formed with the two resilient wires 11 connected in parallel at a tip of the loop opposed to the proximal ends of the resilient wires 11. The tip portion 11a of the resilient wires 11 is deposited in an atmosphere of inactive gas to form a deposited portion A. Further, as shown in FIG. 1, a joint portion B is formed adjacent to the deposited portion A by being jointed with a metallic bonding member 12.

With this structure, the snare loop 10 is allowed to be deformed and tucked into the sheath 1 when the operation wire 2 is withdrawn, and is allowed to protrude from the sheath 1 and expand to its full state due to the resilient property thereof when the operation wire 2 is pushed.

Figure 2:
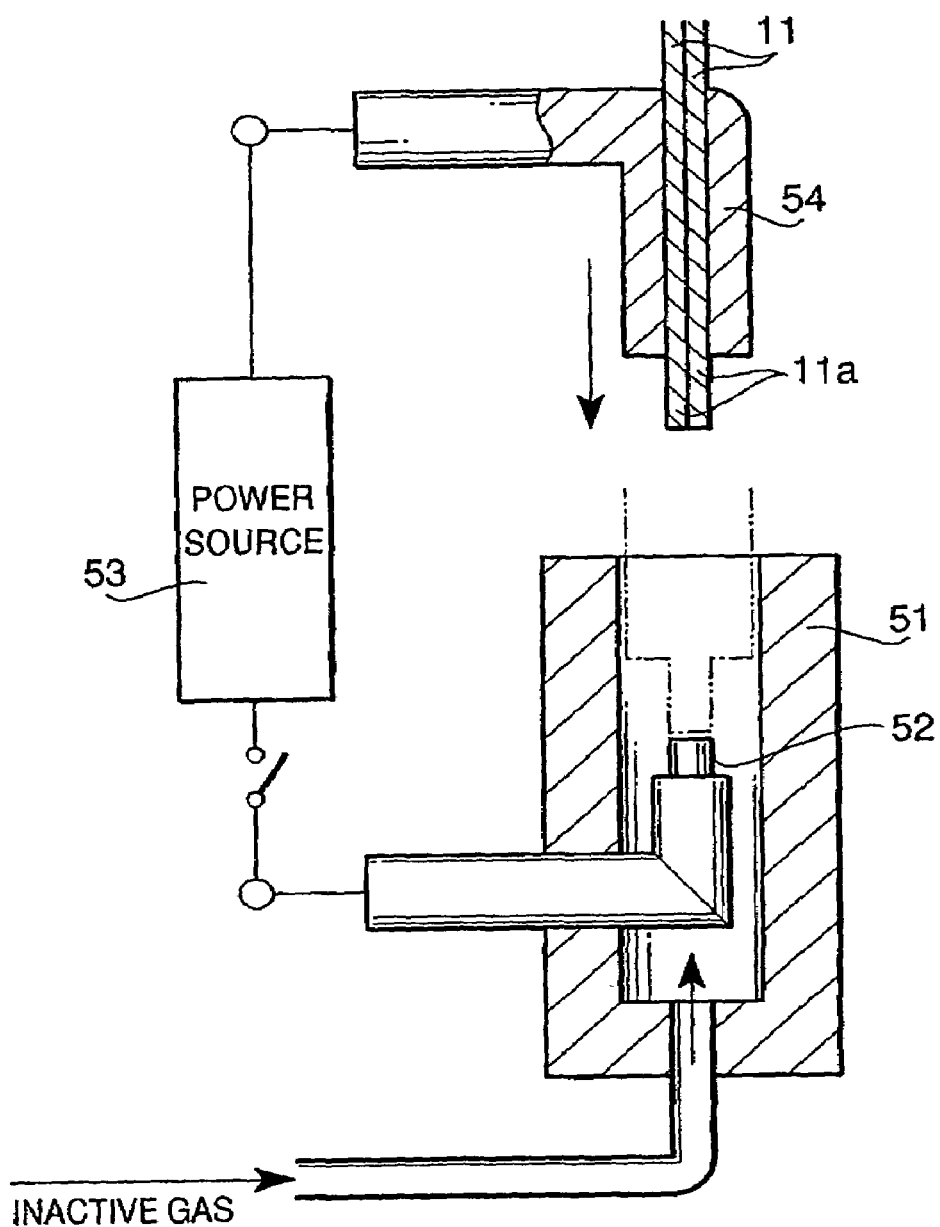
FIG. 2 shows an exemplary producing device for the high-frequency snare used to produce the high-frequency snare in accordance with a method of producing the snare according to the embodiment of the invention.

FIG. 2 shows an exemplary producing device for the high-frequency snare used to produce the high-frequency snare in accordance with a method of producing the snare according to the embodiment of the invention. The tip portion 11a of the resilient wires 11 is deposited inside a cylindrical member 51 wherein inactive gas, for example argon, flows, and an electrode 52 for plasma welding is provided.

With the electrode 52 being electrically conducted with a power source 53, the tip portion 11a of the snare loop 10 is held by a holding member 54 and inserted through an opening into the cylindrical member 51 which is filled with inactive gas as shown with a dashed line. When the electrode 52 and the tip portion 11a become in contact, plasma discharge occurs, and the resilient wires 11 at the tip portion 11a become deposited with each other.

It should be noted that plasma welding carried out in an atmosphere of inactive gas as described above allows the tip portion 11a to be welded solidly without damaging each thin wires of the resilient wires 11.

Figure 3:
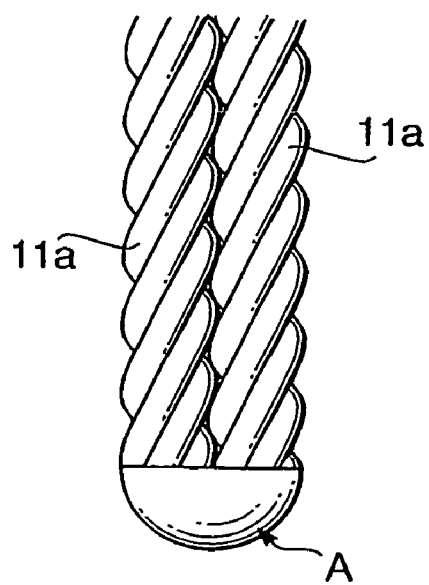
FIG. 3 shows an enlarged side view of the tip portion of the high-frequency snare in the middle of the producing operation.

FIG. 3 shows an enlarged side view of the tip portion 11a of the high-frequency snare when the deposited portion A is formed by plasma welding described as above. In the present embodiment, the deposited portion A is formed to have an approximate shape of a hemisphere. It should be noted that the shape of a hemisphere provides a balance between the dimension and strength of the deposited portion A.

Figure 4:
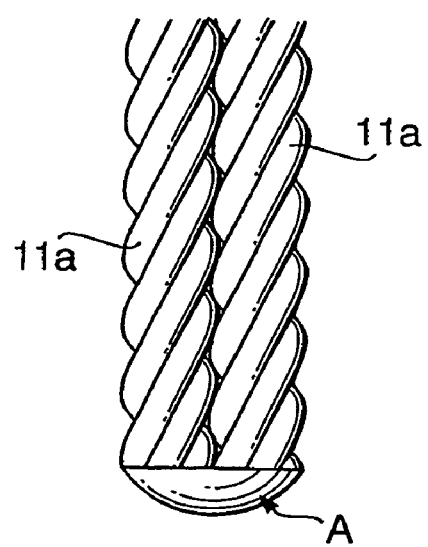
FIG. 4 shows a comparative example of the tip portion of the high-frequency snare in the middle of the producing operation.
Figure 5:
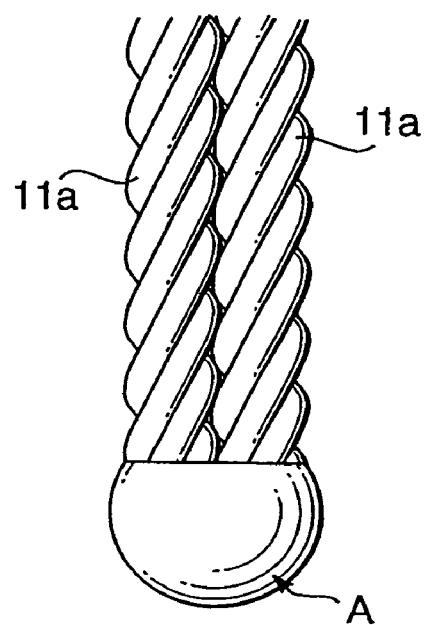
FIG. 5 shows another comparative example of the tip portion of the high-frequency snare in the middle of the producing operation.

FIG. 4 shows a comparative example of the tip portion 11a of the high-frequency snare. When the deposited portion A is formed in a shorter period of time, the deposited portion A is formed to have a convex surface as shown in FIG. 4, which may provide less strength to the deposited portion A against concentrated stress. On the other hand, the deposited portion A is formed in a longer period of time, the deposited portion A is formed to have an approximate shape of a sphere, as shown in FIG. 5. In this case, although the strength at the deposited portion A may be improved, the dimension of the spherical portion becomes greater, which may cause inconvenience when a user performs high-frequency treatment.

Thus, the deposited portion A is enhanced by the plasma welding performed in an atmosphere of inactive gas to have durability against the high temperature due to the sparks at the high-frequency treatment. However, the tip portion 11a adjacent to the deposited portion A becomes brittle due to the high temperature applied during the plasma welding.

Figure 6:
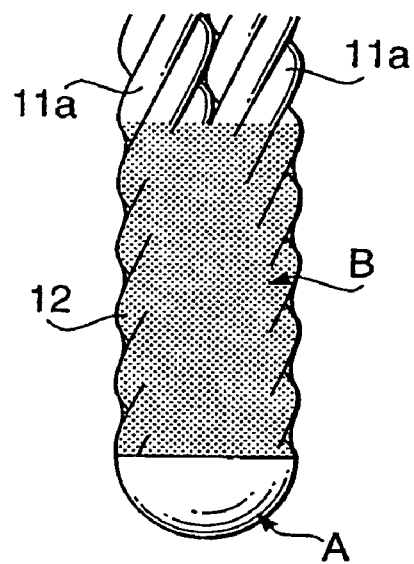
FIG. 6 shows an enlarged side view of the tip portion of the high-frequency snare according to the embodiment of the invention.

In compensation, a portion adjacent to the deposited portion A of the tip portion 11a (i.e., a joint portion B shown in FIG. 6) is jointed with a metallic bonding member 12, for example silver, after the plasma welding process. The bonding process including fusing and cooling silver can be performed in a normal room air. It should be noted that a length of the joint portion B to be jointed should be in or about a range from 1 to 5 mm. With this bonding process, strength of the joint portion B is improved, and the joint portion B is provided with durability against concentric stress which is caused when the mucous membrane is removed.

The silver brazing may be softened by the heat generated due to the sparks at the high-frequency treatment. It should be noted, however, that the tip portion 11a of the two resilient wires 11 which are steadily fixed at the deposited portion A to each other should not disjoint apart. Therefore, unless the silver is melted into liquid to flow, the joint portion B should stay jointed until the temperature of the silver is lowered to the hardening point.

The present invention is not limited to the embodiment described above, and for example, argon as inactive gas may be altered to nitrogen. Also, plasma welding, for example, may be altered to laser welding. Further, silver brazing, for example, may be altered to soldering.

The present disclosure relates to the subject matter contained in Japanese Patent Application No. 2004-257891, filed on Sep. 6, 2004, which is expressly incorporated herein by reference in its entirety.

What is claimed is:

1. A high-frequency snare for an endoscope, comprising:
an electrically insulating sheath;
an operation wire slidably inserted within the sheath; and
a plurality of resilient twisted wires, proximal ends of the plurality of twisted wires being connected to a distal end of the operation wire, distal ends of the plurality of twisted wires being deposited with each other within an atmosphere of inactive gas and connected to each other by plasma welding, a proximal end side of the deposited ends of the plurality of twisted wires being connected to each other with a metallic connector formed by at least one of silver brazing and soldering,
wherein, when the operation wire is operated to withdraw at least a proximal side portion of the plurality of twisted wires, the plurality of twisted wires are configured to be positioned within the sheath, and when the operation wire is operated such that the plurality of twisted wires protrude from the sheath, the plurality of twisted wires are configured to expand to form a resilient loop.

2. The high-frequency snare according to claim 1, wherein the deposited ends of the plurality of twisted wires comprise a generally hemispherical shape.

3. The high-frequency snare according to claim 1, wherein the inactive gas is one of argon and nitrogen.

4. A method of producing a high-frequency snare for an endoscope, the high-frequency snare including an electrically insulating sheath, an operation wire slidably inserted within the sheath and a plurality of resilient twisted wires, proximal ends of the plurality of twisted wires being connected to a distal end of the operation wire, distal ends of the plurality of twisted wires being connected to each other, the twisted wires configured to be positioned within the sheath when the operation wire is operated to withdraw at least a proximal side portion of the plurality of twisted wires, the plurality of twisted wires configured to expand to form a resilient loop when the plurality of twisted wires protrude from the sheath, the method comprising:
depositing the distal ends of the plurality of twisted wires within an atmosphere of inactive gas;
connecting the distal ends of the plurality of twisted wires to each other by plasma welding; and
connecting a proximal end side of the deposited ends of the plurality of twisted wires to each other with a metallic connector formed by at least one of silver brazing and soldering.

5. The method of producing a high-frequency snare according to claim 4,
wherein the inactive gas is one of argon and nitrogen.

\* \* \* \* \*